US010067332B2

(12) United States Patent
Duckett, III

(10) Patent No.: US 10,067,332 B2
(45) Date of Patent: Sep. 4, 2018

(54) OPTICAL RELAY SYSTEM WITH AFOCAL MENISCI ELEMENT

(71) Applicant: Karl Storz Imaging, Inc., Goleta, CA (US)

(72) Inventor: George E. Duckett, III, Castaic, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 180 days.

(21) Appl. No.: 14/933,676

(22) Filed: Nov. 5, 2015

(65) Prior Publication Data
US 2017/0131537 A1 May 11, 2017

(51) Int. Cl.
G02B 13/00 (2006.01)
G02B 23/24 (2006.01)
G02B 27/00 (2006.01)
A61B 1/002 (2006.01)

(52) U.S. Cl.
CPC .......... *G02B 23/2446* (2013.01); *A61B 1/002* (2013.01); *G02B 13/0095* (2013.01); *G02B 23/243* (2013.01); *G02B 27/0025* (2013.01)

(58) Field of Classification Search
CPC ............ G02B 23/2446; G02B 13/0095; G02B 27/0025; G02B 23/243; A61B 1/002
See application file for complete search history.

(56) References Cited

U.S. PATENT DOCUMENTS

| 4,621,910 A | 11/1986 | Takahashi |
| 4,676,606 A | 6/1987 | Takahashi |
| 4,693,568 A | 9/1987 | Takahashi |
| 4,783,154 A | 11/1988 | Takahashi |
| 4,993,817 A | 2/1991 | Hoogland |
| 5,461,509 A | 10/1995 | Canzek |
| 7,515,355 B2 | 4/2009 | Todani et al. |
| 2014/0343362 A1* | 11/2014 | Tesar ..................... A61B 1/002 600/181 |

FOREIGN PATENT DOCUMENTS

| DE | 3838168 A1 | 5/1989 |
| DE | 102005032515 A1 | 1/2007 |
| WO | 2016114081 A1 | 7/2016 |

OTHER PUBLICATIONS

European Search Report Application No. 16197626.1 Completed Date: Mar. 30, 2017; dated Apr. 10, 2017 8 Pages.
(Continued)

*Primary Examiner* — Alicia M Harrington
(74) *Attorney, Agent, or Firm* — Whitmyer IP Group LLC

(57) ABSTRACT

An endoscope is provided having a shaft and an optical system disposed in the shaft. The optical system defines an optical path. The optical system includes a first relay lens and a first meniscus lens positioned in the optical path and between an intermediate image plane and the first relay lens. In one embodiment, a second relay lens and a second meniscus lens, the first relay lens and the first meniscus lens residing on a first side of the intermediate image plane, and the second relay lens and the second meniscus lens residing on a second side of the intermediate image plane, wherein the first and second sides of the intermediate image plane are opposing sides.

18 Claims, 6 Drawing Sheets

(56) References Cited

OTHER PUBLICATIONS

Vrushali R. Korde; et al., Design of a handheld optical coherence microscopy endoscope, Journal of Biomedical Optics Paper 10523RR; revised manuscript; accepted for publication May 4, 2011; published online Jun. 29, 2011, 9 pages.
Rongguang Liang, Optical Design for Biomedical Imaging, Published by SPIE Press, Bellingham, Washington US, 2010, 8 pages.
Jamieson, "Thick meniscus field correctors", Appl Opt. Aug. 1, 1982;21(15):2799. (1 page abstract only).
Rongguang Liang, Optical Design for Biomedical Imaging, Chapter 8: Endoscope Optics, Published by SPIE Press, Bellingham, Washington US, Jan. 24, 2011, vol. PM203, pp. 379-386, 9 pages.

* cited by examiner

OPTICAL RELAY SYSTEM WITH AFOCAL MENISCI ELEMENT

FIELD OF THE INVENTION

The invention relates to rod lens relay systems, which are often employed in medical endoscopes.

BACKGROUND OF THE INVENTION

Relay lenses, such as rod lenses, are often used in endoscopes to relay the image from the objective. A relay lens can include a "relay pair" that includes two rod lenses, and multiple relay lenses can be used to extend the distance from the objective to the image. That is, the length of the shaft of an endoscope can be increased by using relay lenses. Typically, an odd number of relay lenses are used in an endoscope in order to generate a right-side-up image at the eyepiece of the endoscope.

FIG. 1 shows a prior art relay lens 100 comprising rod lens doublets 101 and 102. Rod lenses 101 and 102 reimage an image formed at image plane 103 to image plane 104 along the optical path from the distal end 107 to the proximal end 108 of the relay lens 100. Image plane 103 resides between an objective lens (not shown) and rod lens 101, while image plane 104 resides between rod lens 102 and an eye piece or focusing lens (not shown), either of which can present a final image to a sensor. Alternatively, image planes 103 and 104 can be intermediate image planes which reside between relay lens 100 and additional relay lenses or other optical elements. For example, image plane 103 can be an intermediate image plane containing an image formed by an objective lens or rod lens relay and image plane 104 can contain a further intermediate image or a final image.

Conventional relay lenses contribute large amounts of astigmatism and field curvature to the image. These aberrations have traditionally been corrected in the objective optical elements. However, such correction of the aberrations solely in the objective elements leads to designs that are highly sensitive to tilt and decenter errors caused by manufacturing tolerances. For an endoscope with a large number of relays, the aberrations caused by the stack-up of these tilt and decenter errors in manufacturing tolerances can be too severe to correct solely in the objective elements. In addition, burdening the objective elements with excessive aberration correcting properties can increase the required surface curvatures and/or the optical work done by the objective elements. This can further increase tolerance sensitivity of the system.

There are other ways to compensate for the aberrations in rod lens relays. These include using the eyepiece or a combination of the eyepiece and the relays. Another solution is to design relays with fewer aberrations. U.S. Pat. Nos. 4,676,606, 4,693,568, and 7,515,355 each include information regarding aberration compensation. Many lens system designs require that any aberration correction elements be designed in conjunction with the relay lenses, which restricts the usefulness of the aberration correction elements and increases the cost of designing each lens system.

What is needed, therefore, is a way to effectively correct for aberrations in the relay lenses without over-burdening the objective elements and to reduce the tolerance sensitivity of the lens system. It is further desired to improve the compatibility of aberration correction systems with various rod lens systems.

SUMMARY OF THE INVENTION

It is an object of the invention to more effectively correct for aberrations in a relay lens.

It is a further object of the invention to provide correction for aberrations in rod lens relays that is compatible with rod lens relays of multiple types.

It is a further object of the invention to provide correction for aberrations in rod lens relays in a cost-effective manner.

The foregoing and other objects are at least partially achieved by provision of various embodiments of the present invention. Aberrations in one or more relay lenses are at least partially compensated for by introducing at least one afocal meniscus lens between an image plane and at least one of the relay lenses. Image plane refers to a plane containing an image formed by an element of an optical system. Example elements include, for example, an objective lens and relay lens, such as a rod lens relay (e.g., Hopkins rod-lens system).

According to an aspect of the present invention, an endoscope is provided having a shaft and an optical system disposed in the shaft. The optical system defines an optical path. The optical system includes a first relay lens and a first meniscus lens positioned in the optical path and between an intermediate image plane and the first relay lens.

According to another aspect of the present invention, an optical system for use in an endoscope is provided. The optical system defines an optical path and includes a first relay lens and a first meniscus lens positioned in the optical path and between an intermediate image plane and the first relay lens.

In addition to, or as an alternative to, one or more of the features described above, further aspects of the present invention can include one or more of the following features, individually or in combination:

the optical system includes a second relay lens and a second meniscus lens; the first relay lens and the first meniscus lens reside on a first side of the intermediate image plane; the second relay lens and the second meniscus lens reside on a second side of the intermediate image plane; the first and second sides of the intermediate image plane are opposing sides;

the first and second meniscus lenses are consecutively arranged along the optical path;

the first relay lens has a relay lens pair;

the second relay lens has a relay lens pair;

the relay lens pair has a first rod lens and a second rod lens;

the first meniscus lens is substantially afocal;

the first meniscus lens has a first surface facing the first relay lens and an opposing second surface facing the intermediate image plane, the first surface being convex;

the second meniscus lens has a first surface facing the second relay lens pair and an opposing second surface facing the intermediate image plane, the first surface being convex;

the first meniscus lens has a first surface and an opposing second surface; the first meniscus lens defines a radius, and a thickness extending between the first surface and the second surface; the ratio of the radii of the first surface of the first meniscus lens and the second surface of the first meniscus lens is about 0.75; the ratio of the radius of the first surface to the thickness of the first meniscus lens is about 1.35;

the first meniscus lens has a first surface and an opposing second surface; the first meniscus lens defines a radius, and a thickness extending between the first surface and the second surface; the second meniscus lens has a first surface and an opposing second surface; the second meniscus lens defines a radius, and a thickness extending between the first surface and the second surface; the ratio of the radii of the first surface of the first meniscus lens and the second surface of the first meniscus lens is about 0.75; the ratio of the radius of the first surface to the thickness of the first meniscus lens is about 1.35; the ratio of the radii of the first surface of the second meniscus lens and the second surface of the second meniscus lens is about 0.75; the ratio of the radius of the first surface to the thickness of the first meniscus lens is about 1.35;

an index of refraction of the first meniscus lens is between about 1.7 and about 1.9.

the first meniscus lens is a doublet having a first lens proximal to the intermediate image plane and a second lens distal from the intermediate image plane;

the first lens has a ratio of its radius to a total thickness of the doublet ratio of about 1.55:1 and the second lens has a radius to doublet thickness ratio of about 1.2:1;

the doublet comprises a first lens having an Abbe number of about 47 and a second lens having an Abbe number of about 24;

the optical system has a Hopkins rod lens system; the Hopkins rod lens system including the first relay lens;

the optical system has a Hopkins rod lens system, the Hopkins rod lens system including the first and second relay lenses; and the first lens is a plano-convex lens and the second lens is a plano-concave lens.

These and other aspects of the present invention will become apparent in light of the drawings and detailed description provided below.

An advantage of the present invention is that the afocal meniscus lenses can be used with existing rod lens systems to improve the image quality. Menisci and relay lenses can be mixed and matched for optimum correction of aberrations in the relay lenses. Different designs of afocal meniscus lenses will produce different aberration compensation and correction results.

Other objects, features, and advantages will be apparent from the following detailed description of embodiments of the present invention taken in conjunction with the accompanying drawings. For example, although rod lens relays are shown in the drawings, the present invention includes embodiments utilizing afocal meniscus lens to correct for aberrations in other types of optical relay systems (e.g., a conventional biconvex lens relay system).

DETAILED DESCRIPTION OF THE INVENTION

The invention will now be described in reference to FIGS. 2-7, which show exemplary embodiments of the present invention.

Figure 2:
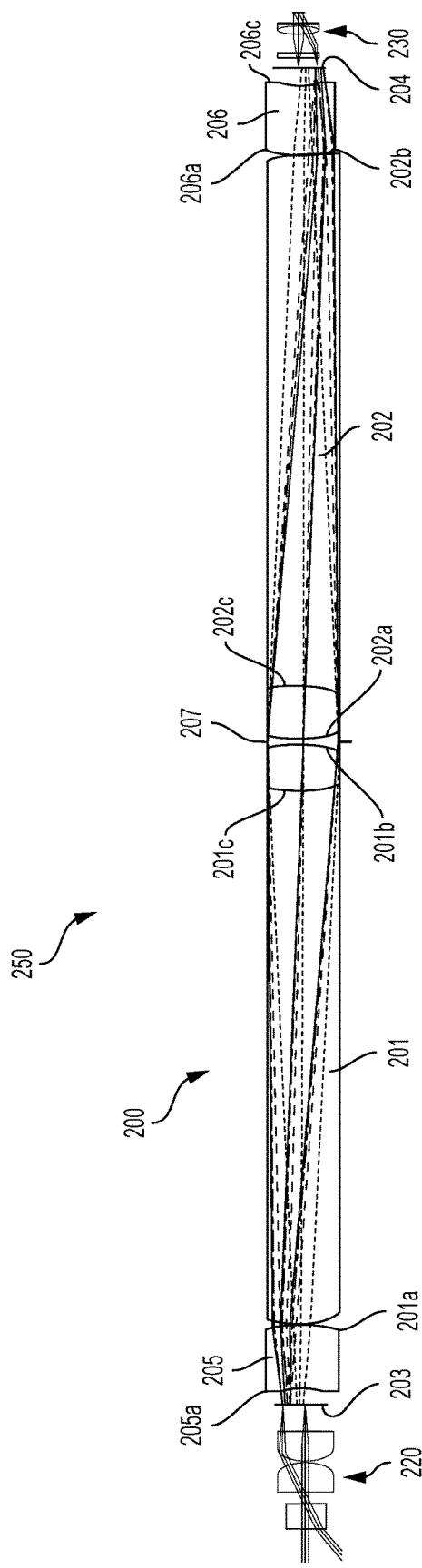
FIG. 2 shows a schematic elevation view of a first embodiment of the invention.

FIG. 2 shows a first exemplary embodiment of an optical system 250 defining an optical path and including a relay lens 200, an objective lens 220 at the distal end of the relay lens 200, and an eyepiece 230 at the proximal end of the relay lens 200. The relay lens 200 includes a first rod lens 201 and a second rod lens 202. In the embodiment shown in FIG. 2, the rod lenses 201, 202 are doublets, which each consist of two simple lenses with a shared surfaces 201c, 202c. In other embodiments, however, rod lenses that consist of only a single lens, or compound rod lenses comprising any number of simple lenses, are used. Between the rod lenses 201, 202 in FIG. 2 is a stop 207. The stop 207 is located in the afocal space of the relay lens 200, in which the rays of the image transmitted through the optical system 250 undergo no substantial net convergence or divergence. In some embodiments, the stop can be an aperture stop. As used herein, "stop" refers to openings or structures that limit ray bundles (e.g., an aperture stop). An aperture stop is a stop that determines the ray cone angle, or equivalently the brightness, at an image point.

In the embodiment of FIG. 2, each rod lens 201, 202 has an image plane 203, 204 associated with it. The respective image planes 203, 204 are on opposite sides of the rod lenses 201, 202. A first meniscus lens 205 is positioned along the optical path between the image plane 203 and the first rod lens 201 and a second meniscus lens 206 is positioned along the optical path between image plane 204 and second rod lens 202.

In the embodiment of FIG. 2, both the rod lenses 201, 202 and the meniscus lenses 205, 206 have distal and proximal surfaces 201a-b, 202a-b, 205a-b, and 206a-b. Rod lenses 201, 202 also have shared surfaces 201c, 202c between the two simple lenses. Further, both the first and second meniscus lenses 205, 206 are substantially afocal. That is, the first and second meniscus lenses 205, 206 are designed so as to produce no substantial net convergence or divergence of collimated light. The meniscus lenses 205 and 206 serve to at least partially compensate for astigmatism and field curvature introduced into the optical system 250 by, for example, the rod lenses 201 and 202.

In some embodiments, including the embodiment shown in FIG. 2, the first meniscus lens 205 and the second meniscus lens 206 can be identical lenses oriented in opposite directions in the relay. Further, the first and second meniscus lenses 205, 206, which are substantially afocal, can be configured to correct aberrations introduced into the system by the rod lenses. These include astigmatism and field curvature.

The ratio of the radii of the curved surfaces for each of the first and second meniscus lenses 205, 206 can be about 0.75 or 3:4. In other embodiments, this ratio can be different and can be varied alongside the other characteristics of the lens, such as its thickness, index of refraction, Abbe number, etc. The characteristics of the meniscus lenses 205, 206 can be selected so that the meniscus lenses 205, 206 are afocal. It is notable that, because the meniscus lenses 205, 206 are afocal, it is possible to use the relay lens 200 to relay an image without the meniscus lenses 205, 206. Likewise, the same meniscus lenses 205, 206 can be used with other rod lens relay designs to compensate for aberrations. The invention thus provides increased flexibility for designers—afocal meniscus lenses of different designs can be mixed and matched with rod lens relays of different designs.

In an embodiment similar to that shown in FIG. 2, the elements of the optical system can have the following characteristics:

| Surface | Radius (mm) | Distance to Next Surface or Thickness (mm) | Index of Refraction | Abbe Number | Outer Diameter (mm) |
|---|---|---|---|---|---|
| Objective | Infinity | 0.6185 | — | — | — |
| First meniscus, distal | −3.2446 | 2.4046 | 1.788 | 47.3 | 1.8 |
| First meniscus, proximal | −4.3062 | 0.1 | — | — | 2.79 |
| First rod lens, proximal | 8.0175 | 19.2 | 1.603 | 38.0 | 2.79 |
| First rod lens, shared | 5.4772 | 1.8 | 1.547 | 53.6 | 2.79 |
| First rod lens, distal | −8.0832 | 0.077 | — | — | 2.79 |
| STOP | Infinity | 0.077 | — | — | 2.79 |
| Second rod lens, distal | 8.0832 | 1.8 | 1.547 | 53.6 | 2.79 |
| Second rod lens, shared | −5.4772 | 19.2 | 1.603 | 38.0 | 2.79 |
| Second rod lens, proximal | −8.0175 | 0.1 | — | — | 2.79 |
| Second meniscus, distal | 4.3062 | 2.4046 | 1.788 | 47.3 | 2.79 |
| Second meniscus, proximal | 3.2446 | 0.6185 | — | — | 1.8 |
| Image | Infinity | — | — | — | — |

In the optical system having the characteristics shown in the foregoing chart, the objective is at the distal end of the relay lens, and each successive surface is the next surface in the proximal direction until the proximal-most image plane is reached. The distances and length measurements are in millimeters.

In the optical system having the characteristics shown in the foregoing chart, the first meniscus lens' distal surface is concave, has a radius of 3.2446 millimeters, an outer diameter of 1.8 millimeters, and is located 0.6185 millimeter from the objective. The thickness of the first meniscus lens is 2.4046 millimeters. The proximal-most surface of the first meniscus lens has a radius of 4.3062 millimeters and an outer diameter of 2.79 millimeters. The first meniscus lens has an index of refraction of 1.788 and an Abbe number of 47.3. The plano-bevel on the distal concave surface of the first meniscus lens is 1.8 millimeters.

The first meniscus lens is 0.1 millimeter from the first rod lens of the relay lens, which has two elements. The distal-most surface of the distal-most element of the first rod lens has a radius of 8.0175 millimeters and is 19.2 millimeters thick. The surface shared by the two elements of the rod lens has a radius of 5.4772 millimeters and is separated from the distal-most surface of the first rod lens by 1.8 millimeters. The proximal most surface of the first rod lens has a radius of 8.0832 millimeters. The distal-most element of the first rod lens has an index of refraction of 1.603 and an Abbe number of 38.0, while the proximal-most element of the rod lens 201 has an index of refraction of 1.547 and an Abbe number of 53.6.

In the optical system having the characteristics shown in the foregoing chart, the stop in the center of the relay lens is 0.077 millimeter from both the first and the second rod lenses. The second rod lens is a mirror image of the first rod lens. Thus, the second rod lens has a first surface with a radius of 8.0832 millimeters, a second surface with a radius of 5.4772 millimeters at a distance of 1.8 millimeters away, and a third, proximal-most surface with a radius of 8.0175 millimeters located 19.2 millimeters away. The indices of refraction and Abbe numbers of the elements of the second rod lens also correspond to those of the first rod lens.

In the optical system having the characteristics shown in the foregoing chart, the second meniscus lens is located 0.1 millimeter from the proximal-most surface of the second rod lens. The distal-most surface of the second meniscus lens has a radius of 4.3062 millimeters and the proximal-most surface has a radius of 3.2446 millimeters. The second meniscus lens has a thickness of 2.4046 millimeters, an index of refraction of 1.788, and an Abbe number of 47.3. The image plane is located 0.6185 millimeter from the second meniscus lens.

Figure 3:
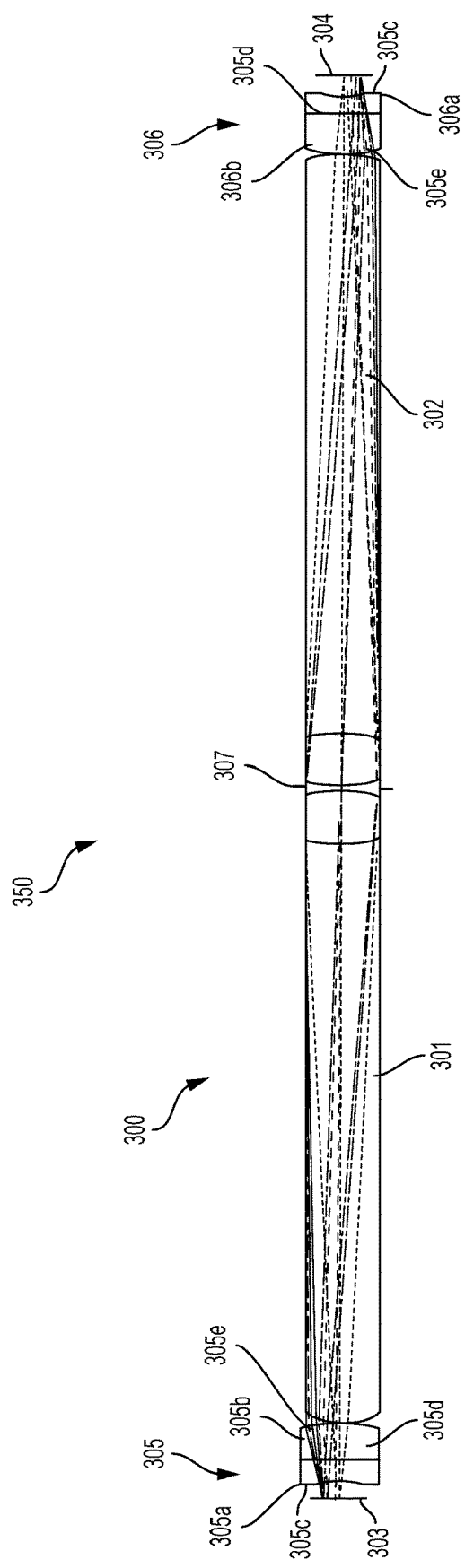
FIG. 3 shows a schematic elevation view of a second embodiment of the invention.

FIG. 3 shows a second embodiment in which the optical system 350 includes an objective lens (not shown), a relay lens 300 that includes two rod lenses 301 and 302, and an eyepiece (not shown). The rod lenses 301 and 302 are doublets, in that they each include two simple lenses with a shared surface. Between the rod lenses 301, 302 is stop 307. A first meniscus lens 305 is disposed between image plane 303 and rod lens 301 and a second meniscus lens 306 is disposed between image plane 304 and rod lens 302.

FIG. 3 shows each of the first and second meniscus lenses 305 and 306 are doublets comprising two simple lenses, as opposed to the single-lensed meniscus lenses of FIG. 2. First meniscus lens 305 comprises a plano-concave lens 305a and a plano-convex lens 305b. These lenses are cemented together or otherwise joined in some embodiments, such that they have a proximal concave surface 305c, a shared surface 305d, and a distal convex surface 305e. Likewise, second meniscus lens 306 comprises a plano-concave lens 306a and a plano-convex lens 306b, with proximal convex surface 306e, shared surface 306d, and distal concave surface 306c. The first and second meniscus lenses 305, 306 are substantially afocal lenses. They are designed so as to produce no substantial net convergence or divergence of collimated light.

The first meniscus lens 305 and the second meniscus lens 306 can be identical doublet lenses, but oriented in opposite directions in the relay. As in the first embodiment shown in FIG. 2, the first and second meniscus lenses 305, 306 of the embodiment shown in FIG. 3 are substantially afocal and configured to correct aberrations introduced into the system by the rod lenses, including astigmatism and field curvature.

The ratio of the radii of the curved surfaces of the first and second meniscus lenses 305, 306 can be about 0.75 or 3:4. In other embodiments, this ratio can be different and can be varied alongside the other characteristics of the lens, such as its thickness, index of refraction, Abbe number, etc. This embodiment shows a design for the afocal meniscus elements including doublets. Numerous other optical designs are possible for use in the present invention, so long as they meet the general requirements of being afocal and a meniscus lens. The meniscus lenses according to the invention can be compound lenses that include more than two lenses, as well.

In an embodiment similar to that shown in FIG. 3, the optical elements can have the following characteristics:

| Surface | Radius (mm) | Distance to Next Surface or Thickness (mm) | Index of Refraction | Abbe Number | Outer Diameter (mm) |
|---|---|---|---|---|---|
| Objective | Infinity | 0.7354 | — | — | — |
| First meniscus, concave | −2.2414 | 0.5 | 1.846 | 23.7 | 1.8 |
| First meniscus, shared | Infinity | 1.384 | 1.788 | 47.3 | 2.79 |
| First meniscus, convex | −2.9286 | 0.1 | — | — | 2.79 |
| First rod lens, proximal | 8.0175 | 19.2 | 1.603 | 38.0 | 2.79 |
| First rod lens, shared | 5.4772 | 1.8 | 1.547 | 53.6 | 2.79 |
| First Rod lens, distal | −8.0832 | 0.077 | — | — | 2.79 |
| STOP | Infinity | 0.077 | — | — | 2.79 |
| Second rod lens, distal | 8.0832 | 1.8 | 1.547 | 53.6 | 2.79 |
| Second rod lens, shared | −5.4772 | 19.2 | 1.603 | 38.0 | 2.79 |
| Second rod lens, proximal | −8.0175 | 0.1 | — | — | 2.79 |
| Second meniscus, convex | 2.9286 | 1.384 | 1.788 | 47.3 | 2.79 |
| Second meniscus, shared | Infinity | 0.5 | 1.846 | 23.7 | 2.79 |
| Second meniscus, concave | 2.2414 | 0.7354 | — | — | 1.8 |
| Image | Infinity | — | — | — | — |

In the optical system having the characteristics shown in the foregoing chart, the objective is at the distal end of the relay lens and each successive surface is the next surface in the proximal direction until the image plane is reached. The distances and length measurements are in millimeters.

The distal surface of the first meniscus lens is located 0.7354 millimeter from the objective of the relay. The distal-most, concave surface of the first meniscus lens has a radius of 2.2414 millimeters. The thickness of the plano-concave lens of the first meniscus lens is 0.5 millimeter. The plano-concave lens has an index of refraction of 1.846 and an Abbe number of 23.7. The thickness of the plano-convex lens of the first meniscus lens is 1.384 millimeters. The convex surface of the meniscus doublet has a radius of 2.9286 millimeters. The plano-convex lens has an index of refraction of 1.788 and an Abbe number of 47.3.

The first meniscus lens is 0.1 millimeter from the distal surface of the first rod lens. The distal-most surface of the distal-most element of the first rod lens has a radius of 8.0175 millimeters and the element is 19.2 millimeters thick. The surface shared by the two elements of the rod lens has a radius of 5.4772 millimeters and is separated from the proximal-most surface of the rod lens by 1.8 millimeters. The proximal most surface of the first rod lens has a radius of 8.0832 millimeters. The distal-most element of the rod lens has an index of refraction of 1.603 and an Abbe number of 38.0, while the proximal-most element of the rod lens has an index of refraction of 1.547 and an Abbe number of 53.6.

The stop in the center of the relay lens is 0.077 millimeter from both the first and second rod lenses. The second rod lens is a mirror image of the first rod lens. Thus, the second rod lens has a first surface with a radius of 8.0832 millimeters, a second surface with a radius of 5.4772 millimeters at a distance of 1.8 millimeters away, and a third, proximal-most surface with a radius of 8.0175 millimeters located 19.2 millimeters away. The indices of refraction and Abbe numbers of the elements of the second rod lens also correspond to those of the first rod lens.

The second meniscus lens is located 0.1 millimeter from the proximal-most surface of the second rod lens. The distal-most, convex surface of the second meniscus lens, has a radius of 2.9286 millimeters. The plano-convex lens has a thickness of 1.384 millimeters, an index of refraction of 1.788, and an Abbe number of 47.3. The concave surface of the plano-concave lens has a radius of 2.2414 millimeters, and the plano-concave lens has a thickness of 0.5 millimeter, an index of refraction of 1.846, and an Abbe number of 23.7. The image plane is located 0.7354 millimeter from the second meniscus lens.

Figure 4:
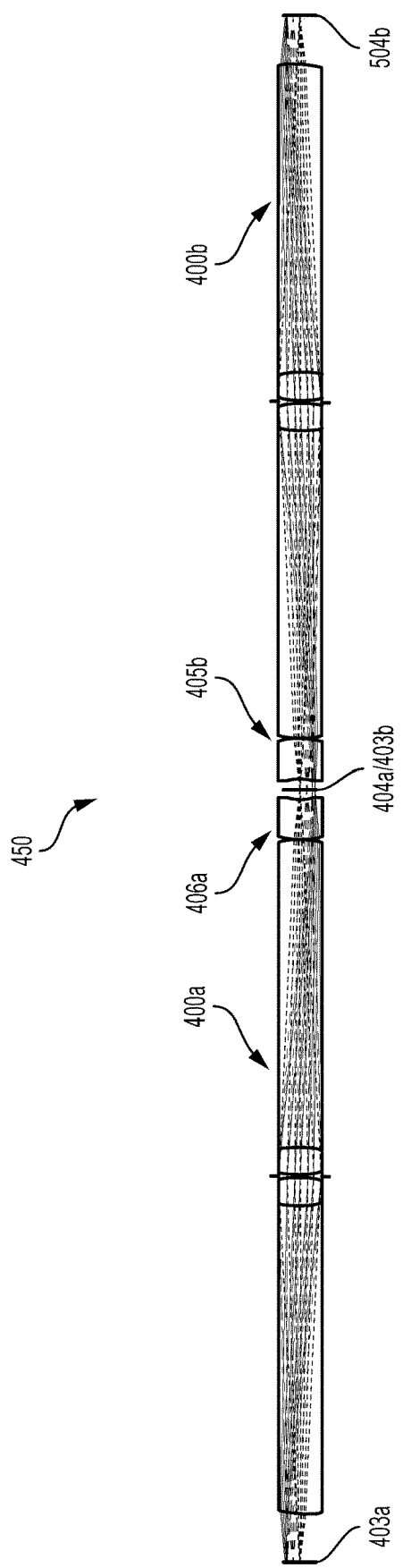
FIG. 4 shows a schematic elevation view of a third embodiment of the invention.

FIG. 4 shows a third exemplary embodiment of the invention in which the optical system 450 includes an objective lens (not shown), relay lenses 400a and 400b, and an eyepiece (not shown). Each of the relay lenses is substantially identical to the relay lens 200 shown in FIG. 2, except for the positioning of the afocal meniscus lenses. A first afocal meniscus lens 406a is disposed between image plane 404a and relay lens 400a. A second afocal meniscus lens 405b is disposed between image plane 403b and relay lens 400b. No afocal meniscus lenses are disposed between image plane 403a and relay lens 400a or between image plane 404b and relay lens 400b. Images planes 403b and 404a may be the same image plane. The afocal meniscus lenses 406a and 405b may be substantially identical to the afocal meniscus lenses described in the embodiment shown in FIG. 2. Alternatively, the afocal meniscus lenses may be doublets, as described in the embodiment shown in FIG. 3.

Figure 5:
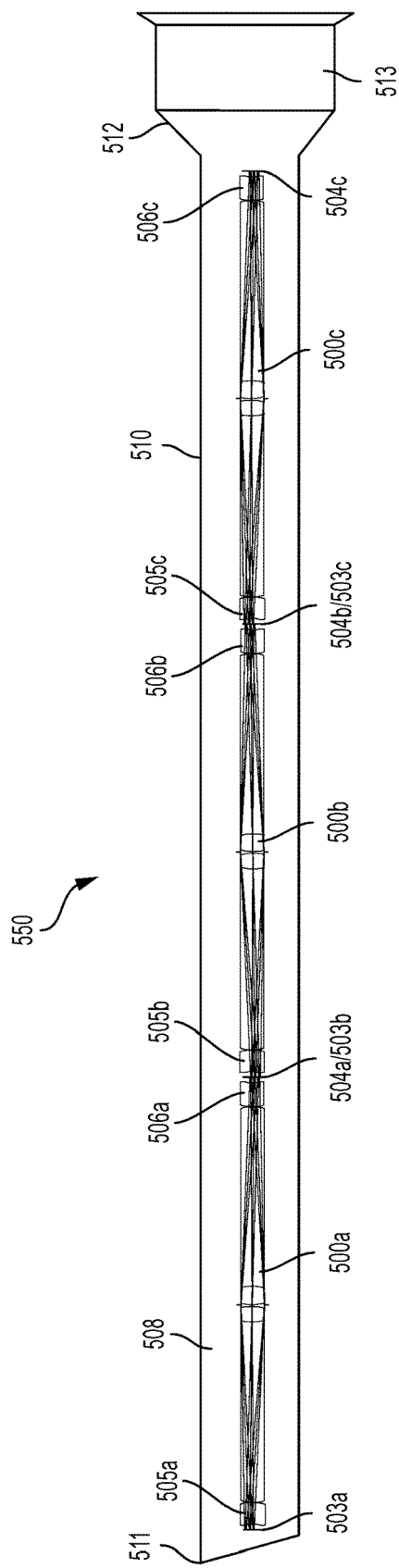
FIG. 5 shows a schematic elevation view of a fourth embodiment of the invention, with an endoscope 510 shown schematically in outline.

FIG. 5 shows an exemplary embodiment of an endoscope 510 with an optical system 550 that has an objective (not shown), three relay lenses 500a, 500b, 500c, and an eyepiece 513. Each of the relay lenses 500a-c includes two afocal meniscus lenses 505a-c, 506a-c disposed between the corresponding image planes 503a-c, 504a-c and the relay lenses 501a-c, 502a-c. All of these optical elements and/or components are disposed in the shaft 508 of the endoscope 510. Each of the relay lenses 500a-c in FIG. 5 are substantially identical to the relay lens 200 shown in FIG. 2. Image planes 504a and 504b, and image planes 504b and 503c may be substantially the same image plane.

It is typical and well within the understanding of those of ordinary skill in the art that the endoscope 510 of FIG. 5 includes additional optical elements for conditioning and transmitting the image from the distal end 511 to the proximal end 512 of the endoscope 510. These often include, for example, a cover glass, objective lens, aperture stops, and field stops. Some embodiments include coupling elements for attaching the endoscope 510 to a camera or other device.

Figure 6:
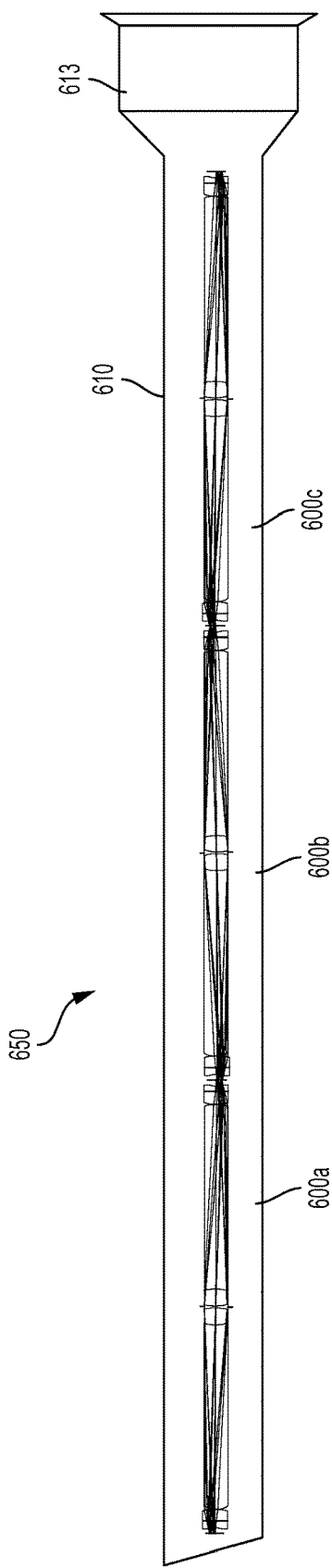
FIG. 6 shows a schematic elevation view of a fifth embodiment of the invention.

FIG. 6 shows an exemplary embodiment of an endoscope 610 with an optical system 650 that has an objective lens (not shown), three relay lenses 600a-c, and an eyepiece 613. The endoscope 610 is similar to endoscope 510 in FIG. 5 except that the afocal meniscus lenses associated with each relay lenses are doublets. Each of the relay lenses 600a-c in FIG. 6 are substantially identical to the relay lens 300 shown in FIG. 3.

Figure 1:
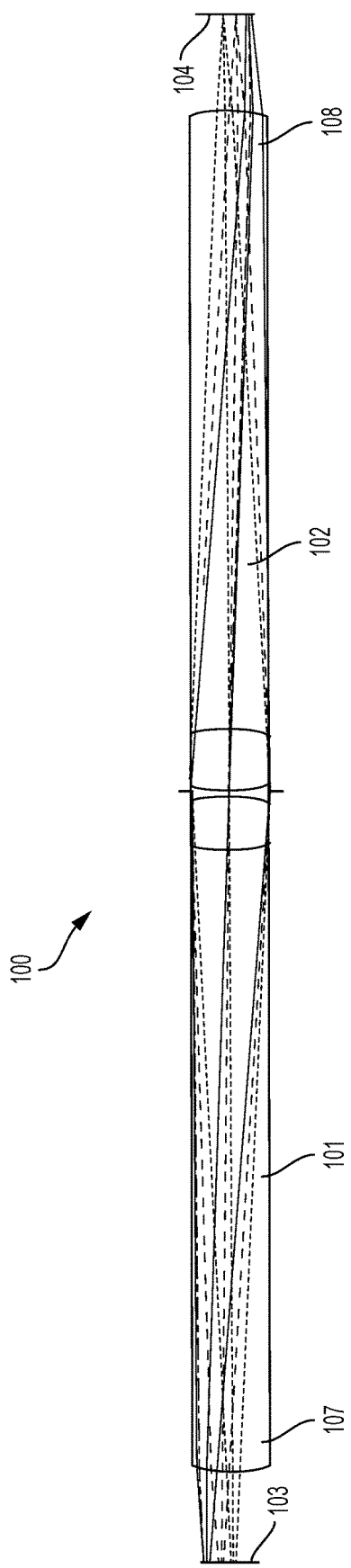
FIG. 1 shows a schematic elevation view of a prior art optical system.
Figure 7:
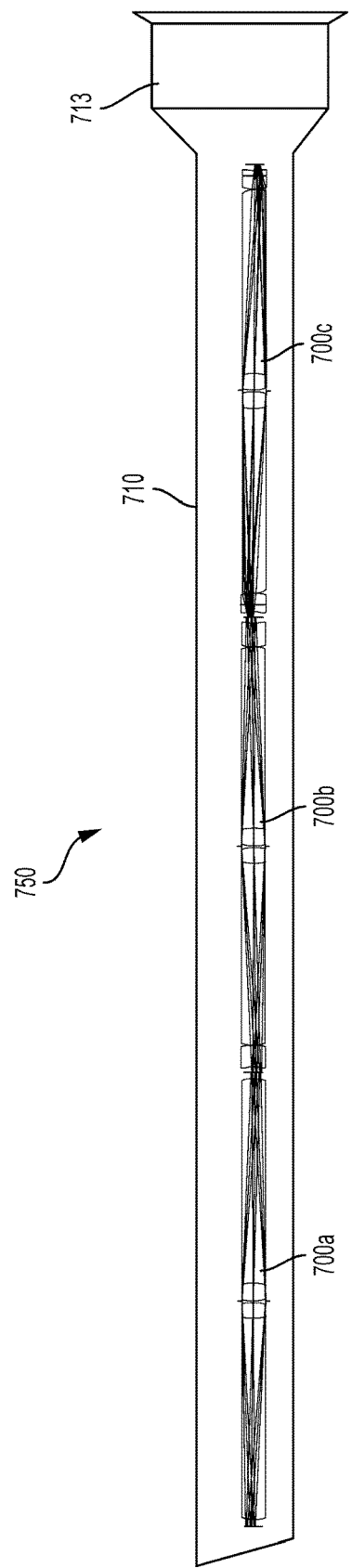
FIG. 7 shows a schematic elevation view of a sixth embodiment of the invention.

FIG. 7 shows an exemplary embodiment of an endoscope 710 with an optical system 750 that has an objective lens (not shown), three relay lenses 700a-c, and an eyepiece 713. The endoscope 710 is similar to the endoscopes 510, 610 in FIGS. 5 and 6, respectively, except that the meniscus lenses associated with each relay lens are of different types. The distal-most relay lens 700a is substantially identical to relay lens 100 shown in FIG. 1, with no afocal meniscus lens. The intermediate relay lens 700b is substantially identical to relay lens 200 shown in FIG. 2, with an afocal meniscus lens. The proximal-most relay lens 700c is substantially identical to the relay lens 300 shown in FIG. 3, with a doublet afocal meniscus lens.

It should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

While several embodiments have been disclosed, it will be apparent to those of ordinary skill in the art that aspects of the present invention include many more embodiments and implementations. Accordingly, aspects of the present invention are not to be restricted except in light of the attached claims and their equivalents. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. An endoscope, comprising:
a shaft; and
an optical system disposed in the shaft, the optical system defining an optical path, the optical system including:
a first relay lens; and
a first meniscus lens positioned in the optical path and between an intermediate image plane and the first relay lens;
wherein the first meniscus lens comprises a first surface and an opposing second surface, and the first meniscus lens defines a radius, and a thickness extending between the first sueface and the second surface; and
wherein the ratio of the radii of the first surface of the first meniscus lens and the second surface of the first meniscus lens is about 0.75 and the ratio of the radius of the first surface to the thickness of the first meniscus lens is about 1.35.

2. The endoscope of claim 1, wherein the optical system further comprises a second relay lens and a second meniscus lens, the first relay lens and the first meniscus lens residing on a first side of the intermediate image plane, and the second relay lens and the second meniscus lens residing on a second side of the intermediate image plane, wherein the first and second sides of the intermediate image plane are opposing sides.

3. The endoscope of claim 2, wherein the first and second meniscus lenses are consecutively arranged along the optical path.

4. The endoscope of claim 2, wherein the second relay lens comprises a relay lens pair.

5. The endoscope of claim 4, wherein the relay lens pair comprises a first rod lens and a second rod lens.

6. The endoscope of claim 2, wherein the second meniscus lens comprises a first surface facing the second relay lens pair and an opposing second surface facing the intermediate image plane, the first surface being convex.

7. The endoscope of claim 2,
wherein the second meniscus lens comprises a first surface and an opposing second surface, and the second meniscus lens defines a radius, and a thickness extending between the first surface and the second surface;
wherein the ratio of the radii of the first surface of the second meniscus lens and the second surface of the second meniscus lens is about 0.75 and the ratio of the radius of the first surface to the thickness of the first meniscus lens is about 1.35.

8. The endoscope of claim 2, wherein the optical system comprises a Hopkins rod lens system, the Hopkins rod lens system including the first and second relay lenses.

9. The endoscope of claim 1, wherein the first relay lens comprises a relay lens pair.

10. The endoscope of claim 9, wherein the relay lens pair comprises a first rod lens and a second rod lens.

11. The endoscope of claim 1, wherein the first meniscus lens is substantially afocal.

12. The endoscope of claim 1, wherein the first meniscus lens comprises a first surface facing the first relay lens and an opposing second surface facing the intermediate image plane, the first surface being convex.

13. The endoscope of claim 1, wherein an index of refraction of the first meniscus lens is between about 1.7 and about 1.9.

14. The endoscope of claim 1, wherein the optical system comprises a Hopkins rod lens system, the Hopkins rod lens system including the first relay lens.

15. An endoscope, comprising:
a shaft; and
an optical system disposed in the shaft, the optical system defining an optical path, the optical system including:
a first relay lens; and
a first meniscus lens positioned in the optical path and between an intermediate image plane and the first relay lens;
wherein the first meniscus lens is a doublet having a first lens proximal to the intermediate image plane and a second lens distal from the intermediate image plane;
wherein the first lens has a ratio of its radius to a total thickness of the doublet ratio of about 1.55:1 and the second lens has a radius to doublet thickness ratio of about 1.2:1.

16. The endoscope of claim 15, wherein the first lens has an Abbe number of about 47 and the second lens has an Abbe number of about 24.

17. The endoscope of claim 15, wherein the first lens is a plano-convex lens and the second lens is a plano-concave lens.

18. An optical system for use in an endoscope, the optical system defining an optical path, the optical system comprising:

a first relay lens; and a first meniscus lens positioned in the optical path and between an intermediate image plane and the first relay lens;

wherein the first meniscus lens comprises a first surface and an opposing second surface, and the first meniscus lens defines a radius, and a thickness extending between the first surface and the second surface; and wherein the ratio of the radii of the first surface of the first meniscus lens and the second surface of the first meniscus lens is about 0.75 and the ratio of the radius of the first surface to the thickness of the first meniscus lens is about 1.35.

\* \* \* \* \*